United States Patent [19]
Claro

[11] Patent Number: 5,810,783
[45] Date of Patent: Sep. 22, 1998

[54] MEDICATION INJECTOR

[76] Inventor: Jorge Antonio Rodrigues Claro, Rua Alfredo Whately, 536, Resende, 27542-170-Resende, Rio de Janeiro, Brazil

[21] Appl. No.: 491,930

[22] PCT Filed: Nov. 16, 1994

[86] PCT No.: PCT/BR94/00037

§ 371 Date: Sep. 1, 1995

§ 102(e) Date: Sep. 1, 1995

[87] PCT Pub. No.: WO95/13839

PCT Pub. Date: May 26, 1995

[30] Foreign Application Priority Data

Nov. 17, 1993 [BR] Brazil ................... PI 9304747

[51] Int. Cl.⁶ ................................ A61M 5/32
[52] U.S. Cl. .............. 604/199; 604/212; 604/262; 604/263; 222/92; 222/103
[58] Field of Search ................. 604/214, 212, 604/232, 187, 257, 259, 262, 263, 185, 199; 222/96, 103, 92; 206/438–439, 277

[56] References Cited

U.S. PATENT DOCUMENTS

| | | |
|---|---|---|
| 798,093 | 8/1905 | Dean . |
| 1,222,814 | 4/1917 | Storz . |
| 2,618,263 | 11/1952 | Lakso et al. . |
| 3,099,264 | 7/1963 | Hubbard . |
| 3,114,369 | 12/1963 | Hall . |
| 3,736,933 | 6/1973 | Szabo . |
| 4,013,073 | 3/1977 | Cunningham . |
| 4,018,222 | 4/1977 | McAleer et al. . |
| 4,130,117 | 12/1978 | Van Eck . |
| 4,475,906 | 10/1984 | Holzner . |
| 4,581,021 | 4/1986 | Landau . |
| 4,692,157 | 9/1987 | Landau . |
| 4,955,871 | 9/1990 | Thomas . |

FOREIGN PATENT DOCUMENTS

11 42 049  9/1957  France .

Primary Examiner—Mark Bockelman
Attorney, Agent, or Firm—Gary M. Nath; Nath & Associates

[57] ABSTRACT

The present invention refers to an easy to use and more cost effective medication injector. The injector comprises a fluid container (1) made, preferably, of one bent, or two straight, edge heat-sealed neutral, flexible, pressure resistant and autoclavable plastic films, containing, at the discharge side, a rigid plastic tube (2) with reinforcement wings (3), in whose distal end is attached a needle (4), tightly enclosed in a plastic tube (5), closed at its distal end (6), the set being enclosed in an air-tight envelope (7) with rims (8). For large volumes infusion, the container (1) is attached to an infusion tubing (9) with a simple drip chamber (40) and an optional clamp (11) and a three-way stopcock (41) adapted to connect a syringe (42) for an initial bolus in a biphasic administration. For large volumes pressure injections, the container (1) is placed between pressing plates (14 and 17) respectively attached to a lower (13) and upper (15) elements, both connected by the main link (16).

2 Claims, 10 Drawing Sheets

FIG. 16

MEDICATION INJECTOR

The present invention refers to a device intended to serve as basic element for a disposable injector for medications or diagnostic solutions, already containing the fluid for injection, ready for use.

BACKGROUND OF THE INVENTION

Presently, therapeutic or diagnostic solutions are administered, mostly, by means of syringes, actuated manually or by means of automated devices, the fluid being transferred to the syringes from glass vials or ampules. Conventional syringes present, however, many recognized disadvantages, as the need to fill the syringe from a separate vial, a cumbersome and time consuming process, including the risk of contamination and, in many cases, the plunger can be difficult to manipulate. In the case of infusion protocols, a bottle or a bag containing the solution to be administered must be connected the infusion tubing, by insertions of tubing spike thru the stopper in the bottle or to the connection in a bag, adding a step to the preparation for use, requiring, also, some degree of dexterity. Many attempts have been made to provide alternative devices to the conventional syringes, to overcome their disadvantages, and also that of the conventional and separately supplyed infusion bags or bottles and infusion tubings.

One type of approach has been to provide an injector system with a pre-filled collapsable reservoir with precisely mesured amounts of medication. These devices have flexible walls, so that its contents can be discharged by compressing or squeezing it. Devices of this type are exemplified in the following U.S. Pat. Nos.:

| U.S. Pat. No. | Patentee |
|---|---|
| 798,093 | Dean |
| 1,222,814 | Storz |
| 2,618,263 | Lakso, et al. |
| 3,099,264 | Hubbard |
| 3,114,369 | Hall |
| 4,013,073 | Cunningham |
| 4,018,222 | McAleer et al. |
| 4,130,117 | Van Eck |
| 4,475,906 | Holzner |
| 4,581,021 | Landau et al. |
| 4,955,871 | Thomas |
| 5,261,881 | Riner |

While the above-listed prior art devices do, in varying degrees, avoid the aforementioned problems associated with plunger-type syringes, they did not found spread application for several reasons, as for example, a lack of providing sufficient physical support for the needle during injection, some present difficulty for self-injection situations, specially for the physically feeble, some present the inability to be used with disposable needles, and also; in devices of this type some mechanism must be included to prevent escape of the fluid during storage before use adding complexicity and cost. Another problem with some devices of the type considered is the difficulty in injecting only a portion of the container volume, due to the tendence of the container wall material to return to its original shape, or memory, in case of relaxation of the pressure applied, resulting in the introduction of air or tissue aspiration. In the case of large volumes injections, there has been a need for systems easy and confortable to operators use, especially in injection procedures requiring extended periods of time. In the same way, there has been also a need for simpler infusion systems, ready for use, decreasing inventory items and adding simplicity.

In the Pat.Appl.PCT/BR94/00007, an injecting device has been proposed, based on a flexible plastic recipient containing the fluid, ready for use. However, in that device, the fluid discharge element, a luer-lock, demands a screw cap to avoid fluid escape before use, as well as the fluid container pressing plates and catchers are made in three separate members causing additional manufacturing difficulties.

Aiming to present a more efficient alternative, easier to use and more cost effective as compared to the conventional systems and other proposed devices as those in the above listed Patents, and also that described in the mentioned Application, by means of a single-acting device, it has been developed the present medication injector.

The invention can be better understood with the detailed description of the attached schedules, being:

DETAILED DESCRIPTION OF THE PREFERRED EMBODIMENTS

Figure 1A:
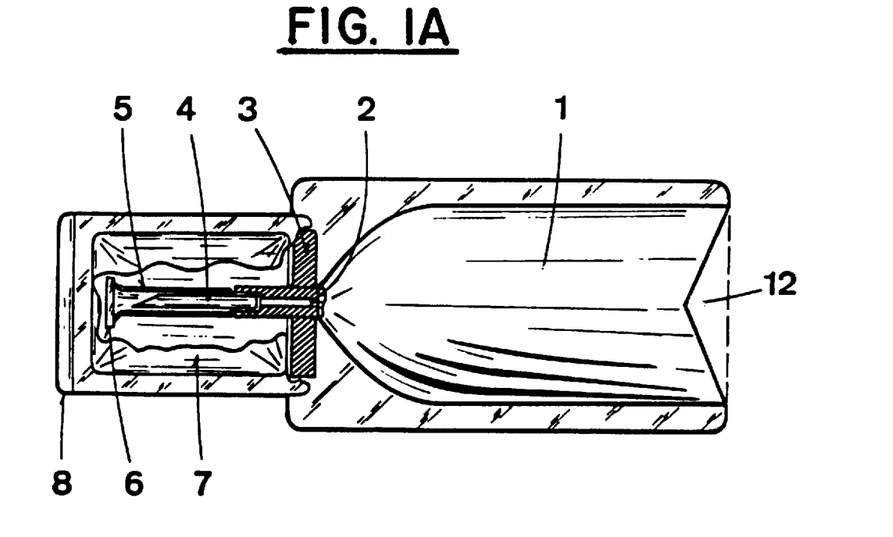
FIG. 1 is an upper plan view of a first embodiment of the present invention.
Figure 1B:
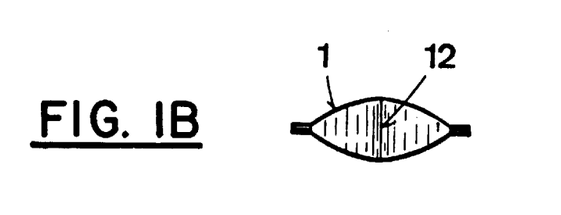

The FIG. 1 illustrates an upper view of the basic element of the device, comprising the fluid for injection container (1) made, preferably, of a bent film of neutral, flexible, pressure resistant and autoclavable plastic material, welded at the edges by heat-sealing process. Opposite to the fluid discharge side it can be made a bend (12) at the container (1) rear-side to decrease the surface area when filled, seen from container (1) rear-side in the detail AA. At the fluid discharge side, it is fixed the rigid plastic ring (2), with reinforcement wings (3), in whose internal distal end, opposite to the container (1) side, is fixed the proximal end of the injection needle (4). To avoid fluid escape during storage before use, the needle (4) is enclosed in a flexible plastic tube (5), closed at its distal end (6) by heat-sealing, to keep air inside the needle (4), acting as a blockage to the fluid. To keep the needle (4) sterility, it, and its closing tube, are enclosed in an air-tight envelope (7), with rims (8) to make its opening easier.

Figure 2:
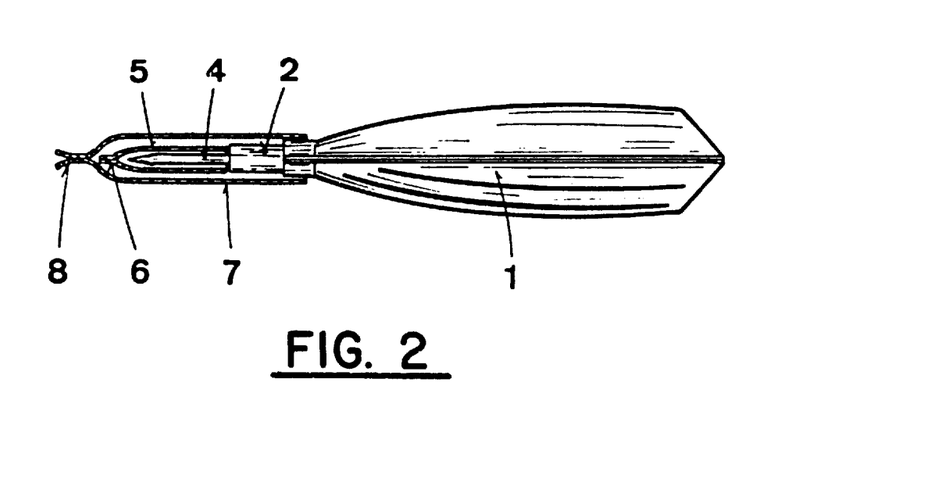
FIG. 2 is a lateral view of the embodiment shown in FIG. 1.

In the FIG. 2 it is observed a lateral view of the container (1) with the needle (4) fixed to the rigid plastic ring (2), the needle (4) enclosing tube (5), the air-tight envelope (7), in a cutaway view, showing the rim (8) to sake its opening easier at the time of use.

Figure 3A:
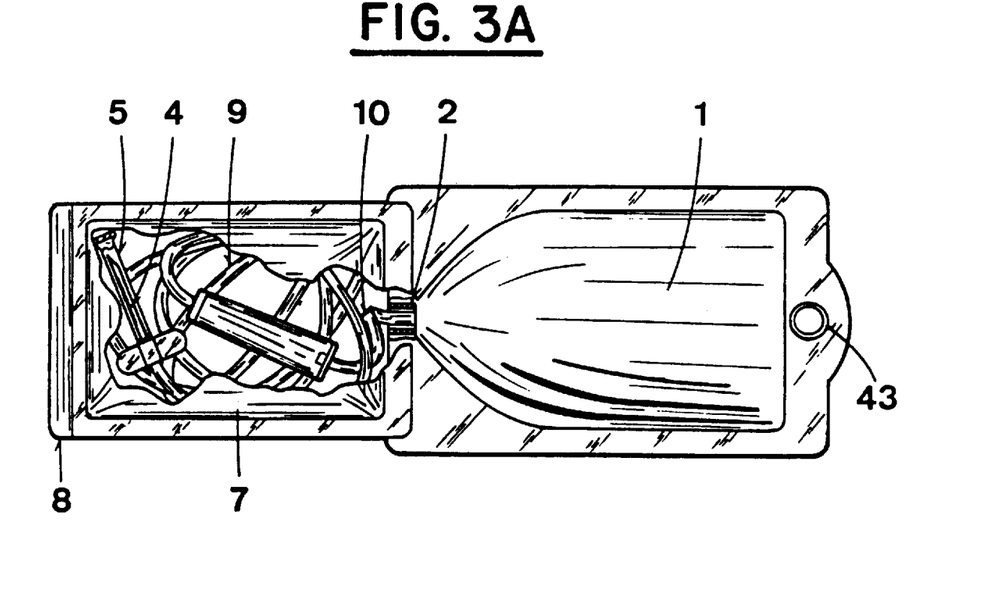
FIG. 3 is an upper view of an alternative embodiment of the present invention.
Figures 3B, 3C:
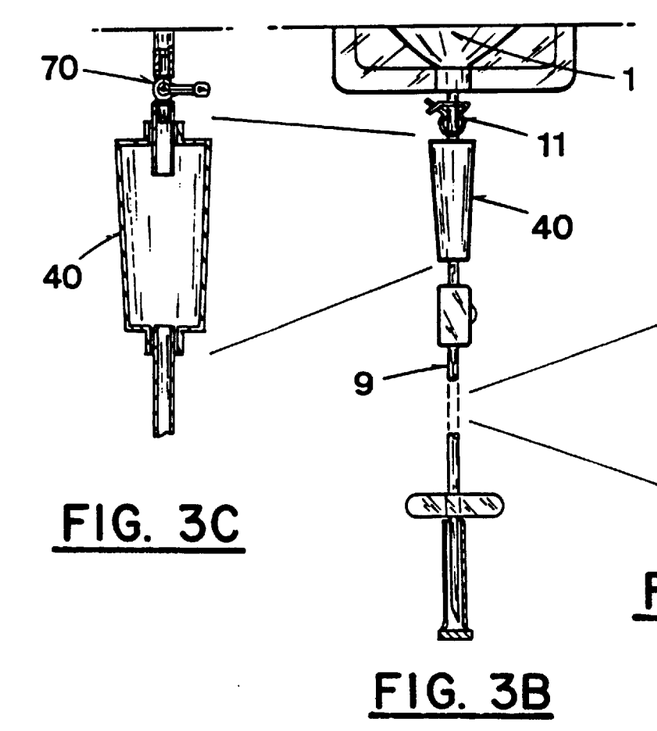
Figure 3D:
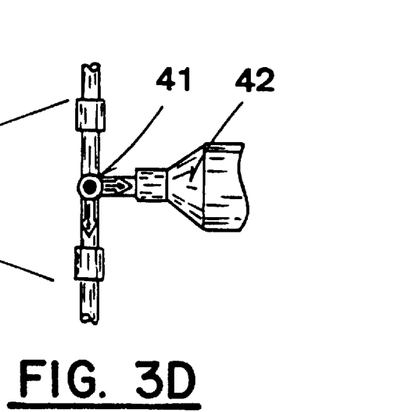

In the FIG. 3 it is illustrated an upper view of a fluid container (1) for large volumes drip infusion, made by sealing of two neutral, flexible, pressure resistant and autoclavable plastic films, in whose fluid discharge side it is now fixed the drip infusion tubing (9), with its proximal and fixed to the internal surface of the rigid plastic ring (2) in the container (1), eliminating the conventional spike. The needle (4) of the infusion tubing (9) is enclosed in the flexible plastic tube (5), closed at its distal end (6), to keep air inside, thus avoiding fluid escape during storage before use. The infusion tubing (9) is enclosed in the air-tight envelope (7) maintaining the internal sterility. For storage inside the envelope (7), containing rims (8), the tubing (9) is bent, additionally avoiding fluid escape from container (1). In the figure, it is noted the bend (10) in the said infusion tubing (9), proximal to the container (1). In the detail BB it is showed the infusion tubing (9) at the time of use, with an optional clamp (11) proximal to the container (1), if desired an additional closure of the said tubing (9), whose drip chamber (40) is simply a cylinder without filter, installed below an optional one-way valve (70), as seen in the detail CC. For bi-phasic fluid administration, the tubing (9) can be attached a three-way stopcock (41) to be adapted a syringe (42), for an initial bolus, as shown in the detail DD. The orifice (43) in the container (1) edge opposite to the infusion tubing (9), for hanging up, completes the set.

Figures 4A, 4B:
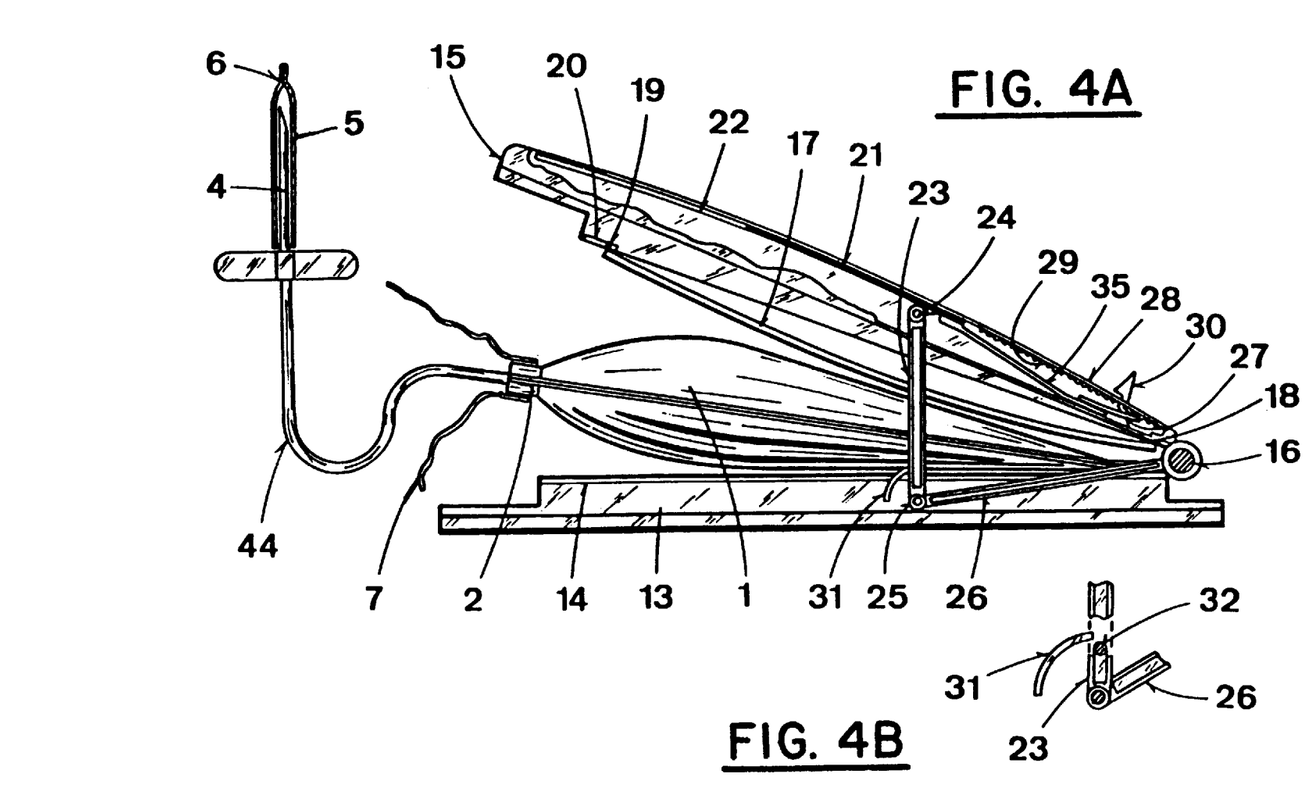
FIG. 4 is a lateral view of a mechanical accessory for pressure injection.

In the FIG. 4 it is illustrated a lateral view of a mechanical accessory for pressure injection of large volumes of fluid, in which it is observed the lower base element (13), with a lower pressure plate (14), connected to an upper pressure element (15) by means of the main link (16). Part of the upper element (15) is the upper pressing plate (17), straight but preferably curved, fixed to the lower face of the element (15), by means of the pin (18) at its posterior end, with its anterior end connected to the lower face of the said element (15), by means of the pin (19), that slides in the guide (20). In the figure, it is also noted the scale blade (21), that slides in the slot (22), that is displaced, on the upper element command, by means of the rod (23), connected to the scale (21 by the pin (24), and connected, by the link (25), to the other rod (26), connected to the main link (16). Once the injection is terminated, with the pressing elements (13) and (15) in contact, their separation, and the scale (21) return to its initial position, and also that of the pin (24), is blocked by means of the curved blade (27), linked to the scale (21), by the arm (35). The extremity of the curved blade (27) contacts the blade (28), containing saliences (29) on its lower length. To liberate the motion, the curved blade (27) end should be pressed against its memory, by means of the angled pin (30). Completing the scale (21) mechanism, there is the arch (31) serving as restrictor, by means of its contact to an internal tappet (32) existing in the rod (23) of scale command shown in the detail EE. Between the lower (13) and the upper (15) pressing elements, it is installed the fluid container (1), for large volumes injections, linked to an injection tubing (44), by the rigid plastic ring (2). The injection tubing (44) is maintained, on storage before use, in the air-tight envelope (7), opened in the figure to indicate a preparation for injection. Also, its needle (4) is enclosed in the plastic tube (5) closed at its distal end (6) to keep air inside the tubing, avoiding fluid escape during storage.

Figures 5A, 5B, 5C:
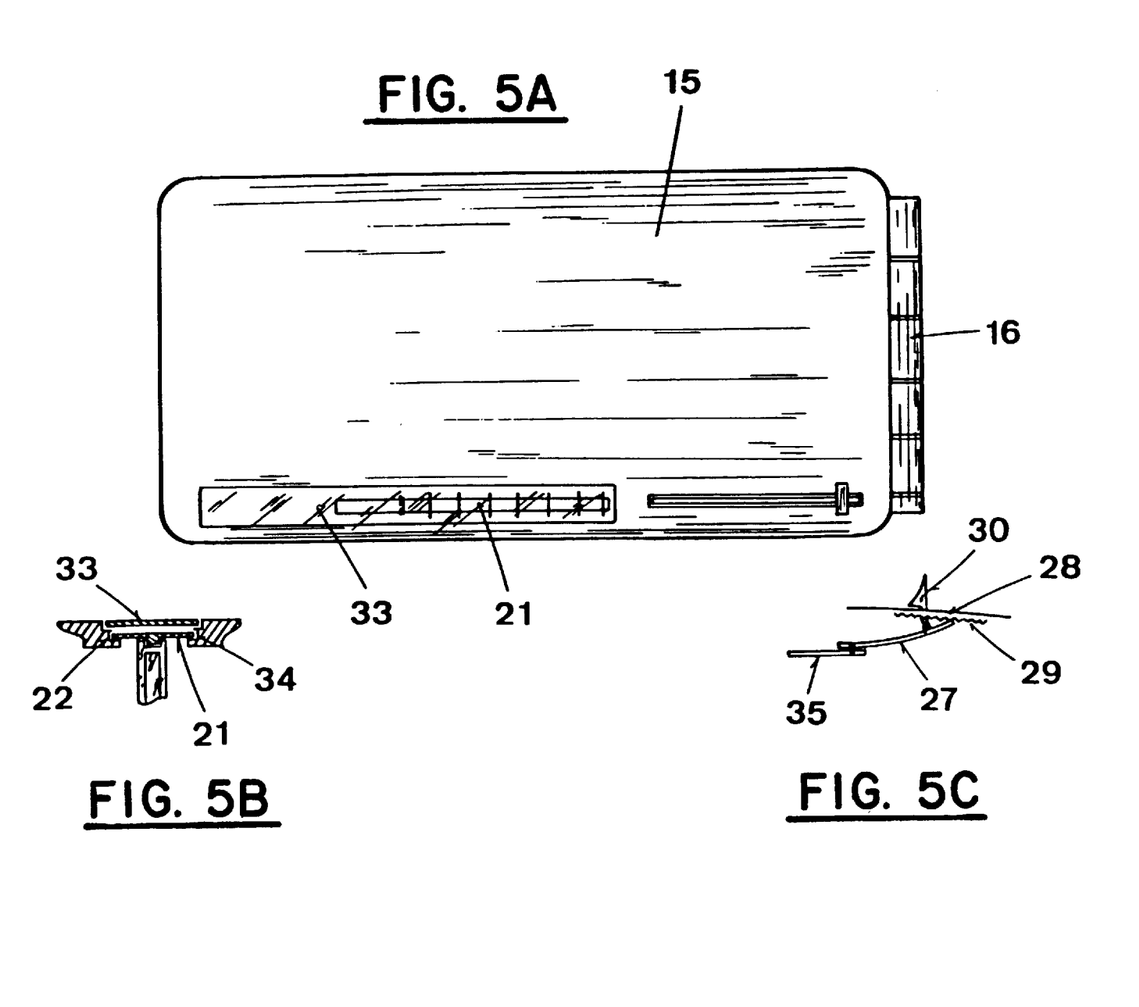
FIG. 5 is an upper view of the pressing mechanism for large volume injections.

In the FIG. 5 it is Illustrated an upper view of the pressing mechanism for large volumes injections, in which it is observed the scale (21), under the transparent blade (33), seen frontally in the detail FF, being noted that the scale (21) slides in the guides (22) and (34). The scale blade (21) is connected to the locking curved blade (27), by means of the rod (35) sliding under the blade (28) with saliences (29) on its lower face, whose contact is better observed in the detail GG, in which it is detached the curved blade (27), the saliences (29) of the blade (26) and the angled pin (30).

Figure 6:
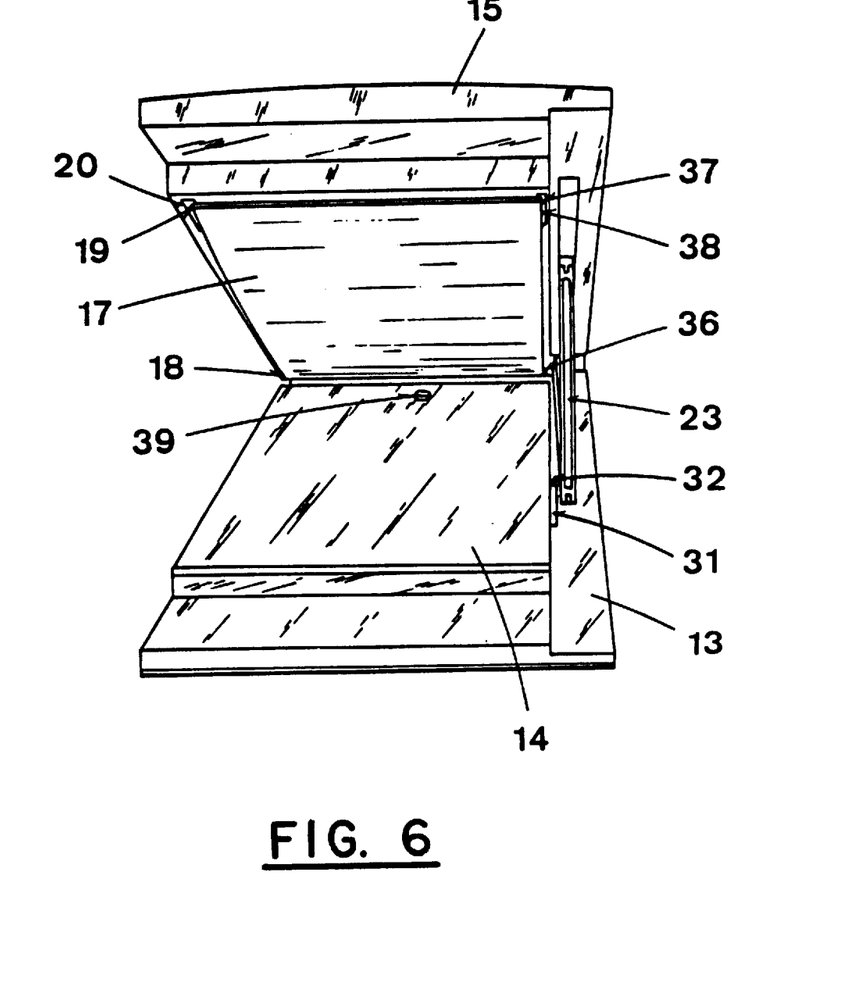
FIG. 6 is a frontal view of the pressing mechanism.

The FIG. 6 illustrates a frontal view of the pressing mechanism, in which it is noted that the upper pressing blade (17) has two pins (18) and (36), in its posterior and, and other two pins (19) and (37), that slide in the guide slots (20) and (38) at the anterior portion of the element (15). In the figure, it is noted the rod (23) having the internal tappet (32) in contact with the limiting arch (31), that exists in the side of the element (13). The saliene (39) existing on the lower pressing plate (14) of the base element (13) is intended to fit in the orifice (43) of the container (1).

Figure 7A:
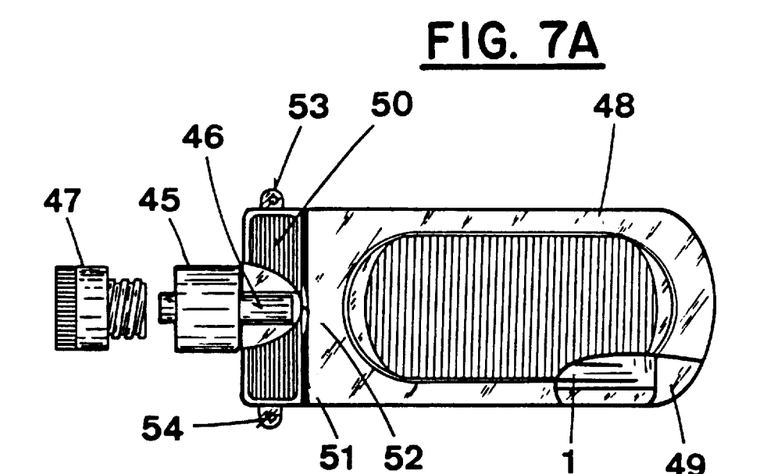
FIG. 7 is an alternative embodiment of the present invention shown in an upper view.
Figure 7B:
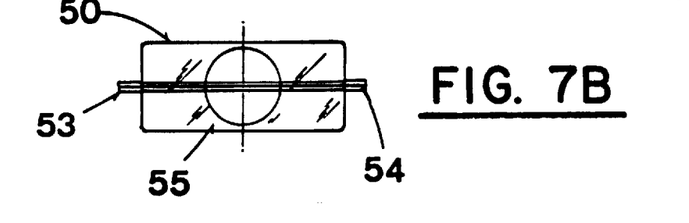

In the FIG. 7 it is depicted a model of the proposed medication injector, in an upper view in a variant containing a luer-lock (45) made molded together with the rigid plastic ring (46), with its cap (47). It is observed, also, part of the recipient (1) placed between the two pressing plates (48) upper and (49) lower, the upper catcher (50) linked to the plate (48) by a link (51) at the borders but not at the center (52), and the two elements (53) right and (54) left, to keep the catchers in contact and fixed, as shown in the detail HH, where is depicted, in a frontal view, the catchers (50) upper and (55) lower.

Figure 8A:
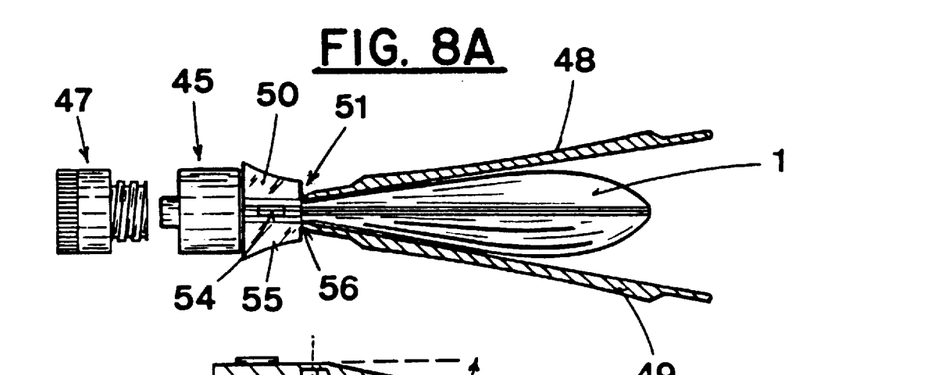
FIG. 8 is a lateral view of an injector installed between pressing plates.
Figure 8B:
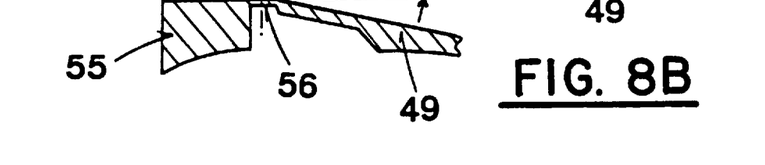

FIG. 8 illustrates a lateral view of the injector, showing the fluid container (1) installed between the pressing plates (48) upper and (49) lower, the catchers (50) upper and (55) lower, behind the luer-lock (45), for needle adaption, and its cap (47). It is also depicted a representation of the upper and lower pressing elements, where it can be noted that they are made of two molded pieces, with the catcher (50) and the pressing plate (48), upper, as one piece with the intermediary length (51) flexible, constituting the upper element, and the catcher (55) and the pressing plate (49), lower, as one piece with the intermediary length (56), flexible, as the lower element. The catchers (50) upper and (55) lower, are kept in tight contact with the frontal edge of the container (1) by means of the welded link (54) showed, and the link (53) not visible in the figure. The detail II show, more clearly, a section of the lower element, equal to the upper, showing the catcher (55), linked, forming one molded piece, to the pressing plate (49) and the intermediary length (56).

Figure 9:
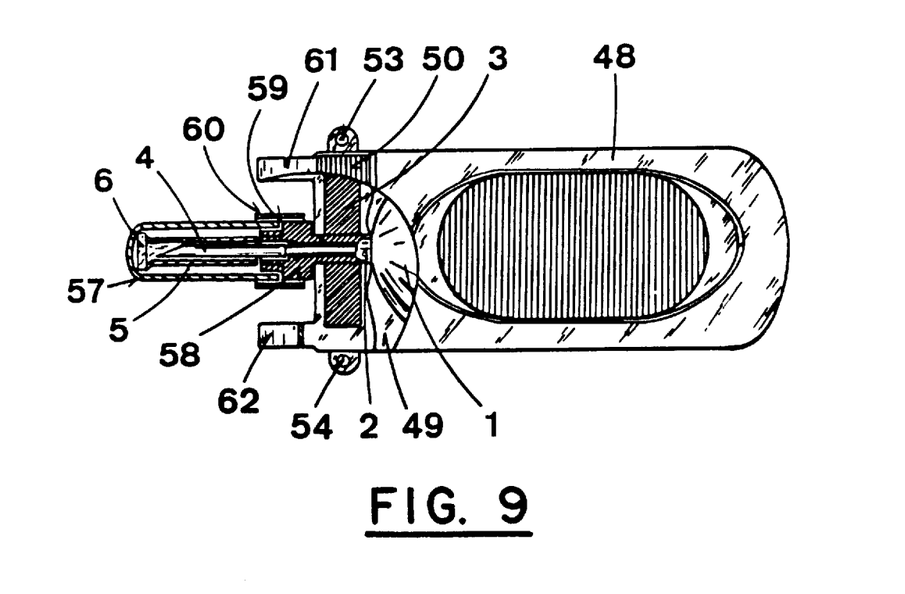
FIG. 9 is an alternative embodiment of the present invention seen from a top view.

In the FIG. 9 it is illustrated another variation of the device, whose injection needle (4) linked to the rigid plastic ring (2) with reinforcement wings (3) and enclosed in the plastic tube (5) closed at its distal end (6), are enclosed in an external plastic tube (57), to maintain internal sterility. To accomplish this, the cap (S7) is threaded, preferably, in a ring set (58) molded one piece with the ring (2), whose contact (59) is covered, preferably, by an adhered ribbon (60) to garantee additional safety for sterility. In the figure, it is also noted the container (1) installed between the pressing plates (48) upper and (49) lower, a section of the upper catcher (50) and the catchers contact fixing elements (53) right and (54) left. It also can be noted that in this model, the upper and lower pressing sets are now made one molded piece, with the upper and lower pressing elements linked by the bent elements (61) right and (62) left, to facilitate the manufacturing process.

Figure 10:
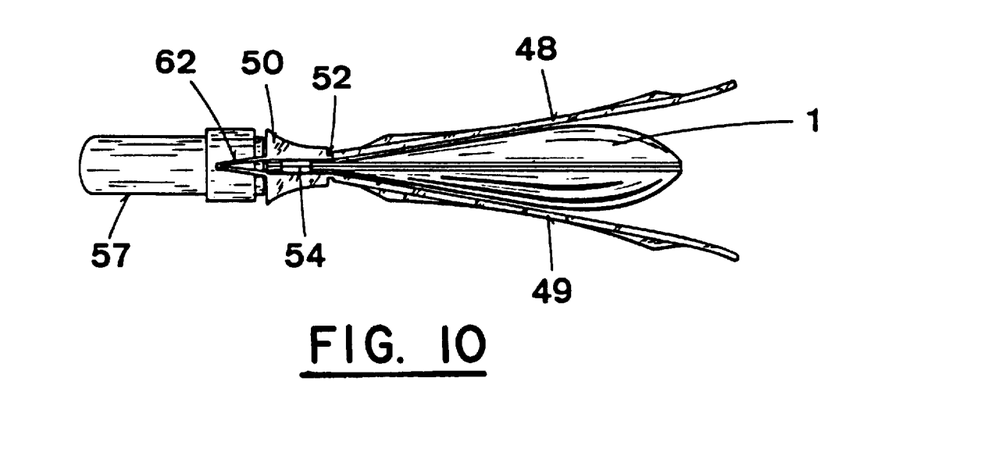
FIG. 10 is a lateral view of an injector between pressing plates.

The FIG. 10 illustrates the injector device in a lateral view, showing the fluid container (1) between the pressing plates (48) upper and (49) lower, as one piece with the catchers (50) upper and (55) lower, the element (54) left, to maintain the catchers joined, the needle set external cap (57) and the upper and lower pressing elements left link (62).

Figure 11:
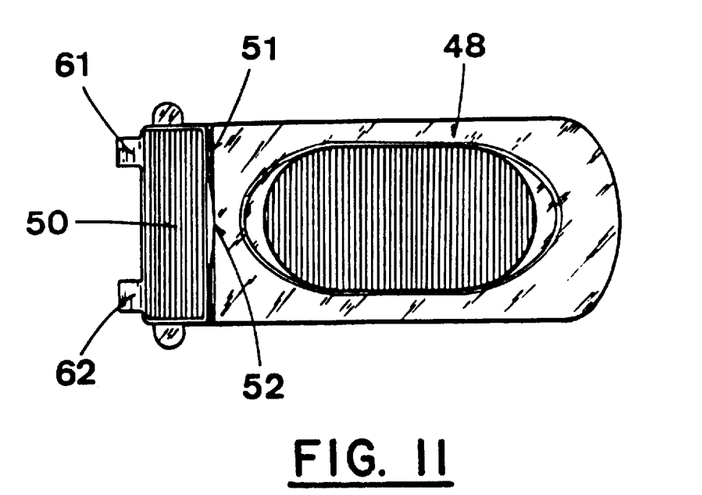
FIG. 11 is an upper view of the pressing plates.

The FIG. 11 depicts an upper view from the pressing element upper, showing the upper pressing plate (48), the upper catcher (50), made one piece with the intermediary (51), with a blank spacing (52) and the bent links (61) right and (62) left.

Figure 12:
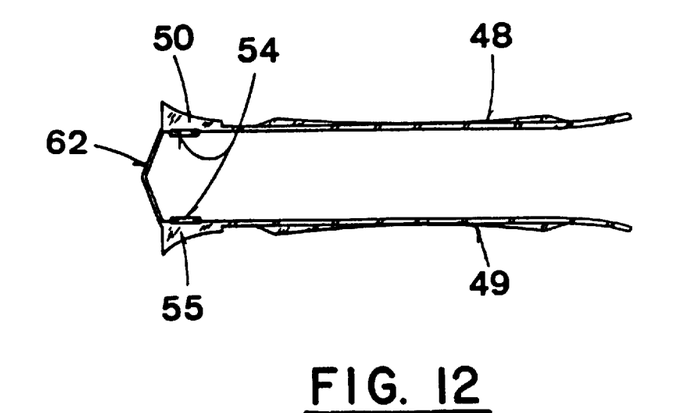
FIG. 12 is a side view of the pressing set.

In the FIG. 12 it is illustrated a representation of the pressing set, being observed that the upper catcher (50) and pressing plate (48) are made one piece with the lower catcher (55) and pressing plate (49), straight when not installed on the fluid container (1), linked by the elements (61) right and (62) left, as one piece with the catchers (50) upper and (55) lower.

Figure 13:
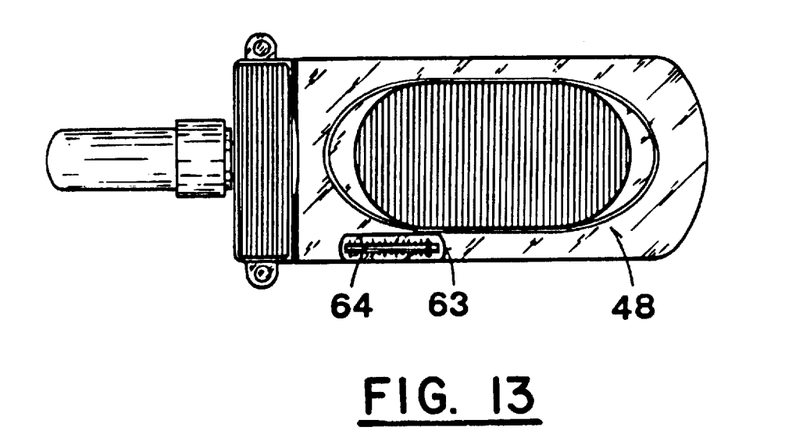
FIG. 13 is an upper view of an alternative embodiment of the present invention.

The FIG. 13 illustrates the injector device in an upper view, with a scale for injected volume and speed monitoring, located at sides of the upper pressing plate (48), being observed the scale window (63) with a slot (64) in which slides the scale needle (65), indicating the injected volume.

Figure 14:
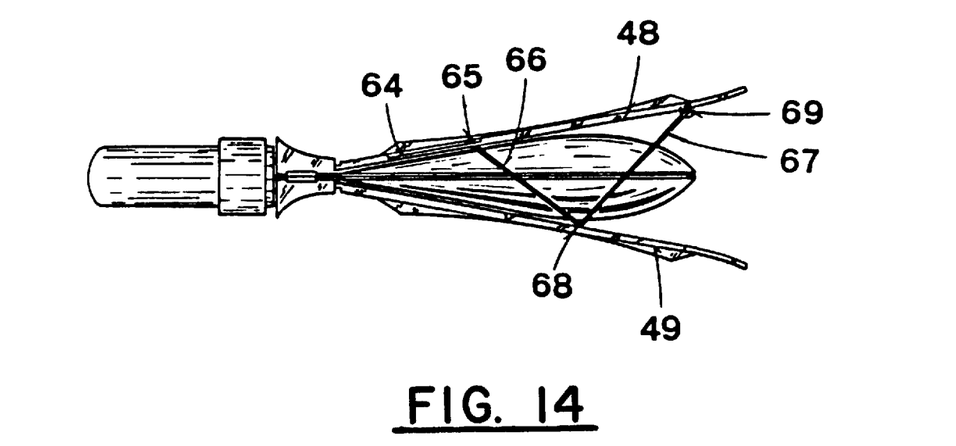
FIG. 14 is a lateral view of an injector.

In the FIG. 14 it is depicted a lateral view of the medication injector, being observed the scale needle (65) at the end of the command rod (66) operating linked to another rod (67), with the rods (66) and (67) being linked by the link (68), just resting on the upper face of the lower pressing plate (49), being the extermity of the rod (67), opposite to the link (68) pivoting around the link (69) fixed to the lower face of the upper pressing plate (48). At the moment of injection, the pressure applied on the plates (48) and (49) makes them to approach each other, forcing the rods (66) and (67) to rotate, making the scale needle (65), at the end of the rod (66) to slide in the scale slot (64) indicating the injected volume.

Figure 15A:
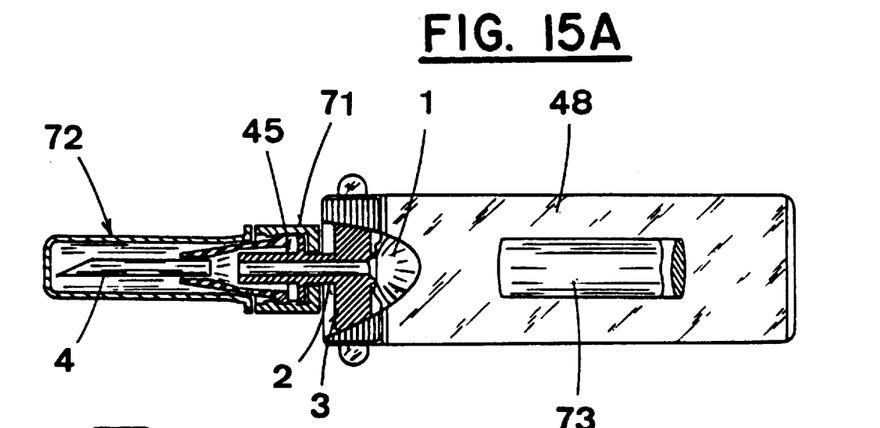
FIG. 15 is an upper view of an alternative embodiment.
Figure 15B:
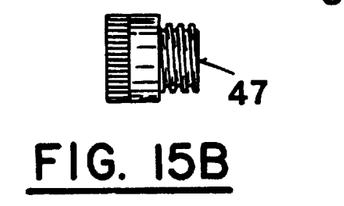

In the FIG. 15 it is illustrated an upper view of a variation of the proposed device, now intended for fluid aspiration purposes, containing a luer-lock (45) with its semi-free ring (71), connected to the needle (4) and a dust guard (72), the rigid plastic ring (2) with reinforcement wings (3), the now empty container (1), under the upper plate (48) with its handle (73), When the aspiration is terminated, the needle is withdrawn and the luer-lock cap (47) closes the device, to protect the content from contamination.

Figure 16:
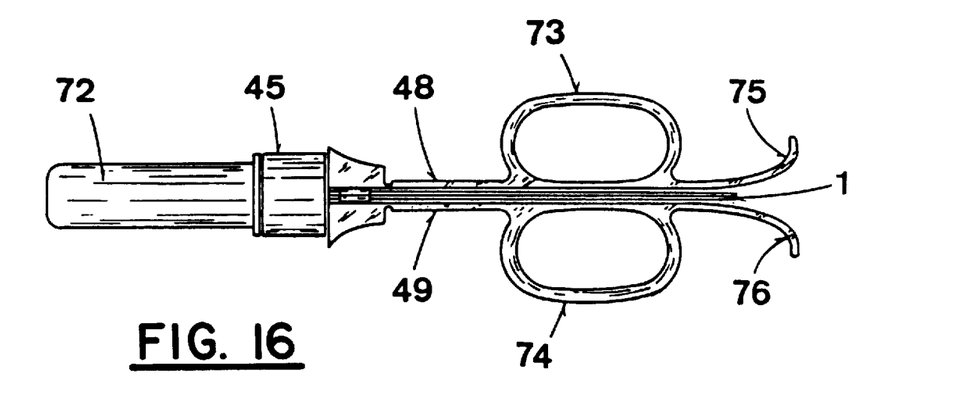
FIG. 16 is a lateral view of the device shown in FIG. 15.

FIG. 16 illustrates a lateral view of the device in its aspiration arrangement, being observed the now empty container (1) between, and with its upper and lower surfaces firmly glued to, the lower face of the upper plate (48) and to the upper face of the lower plate (49), having handles (73) fixed at the surface of the plate (46). upper and (74) at the surface of the plate (49) lower. The extremities, opposite to the luer-lock (45), respectively (75) of the upper plate (48), and (76) of the lower plate (49), are made curved and perpendicular to the longitudinal axis of the device, to facilitate a vertical resting position when filled with the aspirated fluid.

Although the invention has been described and detailed in accordance with the concretions here inserted, many modifications and variances can be made on it, according to the attached claim.

I claim:

1. A medication injector, comprising:
    a fluid container having a discharge end, said container formed of a folded plastic film sealed along its edges forming a fluid compartment;
    a rigid ring fixed at the discharge end of said container and in communication with said fluid compartment, said ring having reinforcement wings;
    a injection needle having proximal and distal ends, fitted at said proximal end to said rigid ring and thereby being in fluid communication with said fluid compartment;
    a plastic tube sealed at its distal end, tightly enclosing said injection needle, and acting to prevent leakage of liquid through said distal end of said injection needle; and
    a protective envelope formed around said injection needle and said plastic tube.

2. A medication injector, comprising:
    a fluid container having a discharge end, said container formed of a folded plastic film sealed along its edges to form a fluid compartment;
    a rigid ring fixed at the discharge end of said container forming an opening into said fluid compartment;
    drip infusion tubing fitted at a first end to said rigid ring and thereby being in fluid communication with said fluid compartment;
    an injection needle having proximal and distal ends, fitted at said proximal end to a second end of said drip infusion tubing, thereby being in fluid communication with said fluid compartment;
    a plastic tube sealed at its distal end, tightly enclosing said injection needle, and acting to seal said distal end of said injection needle; and
    an airtight envelope formed around said injection needle, said plastic tube and said drip infusion tubing.

* * * * *